United States Patent
Specht et al.

(10) Patent No.: US 9,072,908 B2
(45) Date of Patent: Jul. 7, 2015

(54) ACTIVE IMPLANTABLE DEVICE

(75) Inventors: Heiko Specht, Hanau (DE); Andreas Reisinger, Alzenau (DE); Klaus Ruppert, Maintal (DE); Alfred Hohmann, Schmitten (DE)

(73) Assignee: Heraeus Precious Metals GmbH & Co. KG, Hanau (DE)

( * ) Notice: Subject to any disclaimer, the term of this patent is extended or adjusted under 35 U.S.C. 154(b) by 1057 days.

(21) Appl. No.: 13/068,974

(22) Filed: May 25, 2011

(65) Prior Publication Data
US 2011/0293866 A1 Dec. 1, 2011

(30) Foreign Application Priority Data

May 25, 2010 (DE) .......... 10 2010 021 381
Apr. 11, 2011 (DE) .......... 10 2011 016 702

(51) Int. Cl.
| | | |
|---|---|---|
| B32B 1/02 | (2006.01) | |
| A61N 1/00 | (2006.01) | |
| B29C 65/00 | (2006.01) | |
| B32B 27/00 | (2006.01) | |
| A61N 1/375 | (2006.01) | |
| C09J 4/06 | (2006.01) | |
| C08J 5/00 | (2006.01) | |
| C09J 133/08 | (2006.01) | |

(52) U.S. Cl.
CPC .......... *A61N 1/3752* (2013.01); *Y10T 156/10* (2013.01); *Y10T 428/1352* (2013.01); *C08J 5/00* (2013.01); *C09J 133/08* (2013.01); *Y10T 428/13* (2013.01); *Y10T 428/1355* (2013.01); *C09J 4/06* (2013.01)

(58) Field of Classification Search
CPC .......... A61N 1/13752; Y10T 425/1352; Y10T 156/10; C08J 5/00; C09J 133/08
USPC .......... 428/34.1, 35.7, 35.8; 607/5; 156/60, 156/275.5, 332
See application file for complete search history.

(56) References Cited

U.S. PATENT DOCUMENTS 6,006,133 A * 12/1999 Lessar et al. .......... 607/5

OTHER PUBLICATIONS

Germano, J.J., Darge, A., Maisel, W.H., "Weakened ICD Header Bond: Abnormality Not Limited to Subpectoral Implants," Heart Rhythm, 2010. doi:10.1016/j.hrth.m.hrthm.2010.01.041, pp. 701-704.
Germano, Joseph J., et al., "Weakened Implantable Cardioverter-Defibrillator Header Bond: Abnormality Not Limited to Subpectoral Implants," Heart Rhythm, vol. 7, No. 5, pp. 701-704 (May 2010).

* cited by examiner

*Primary Examiner* — Walter B Aughenbaugh
(74) *Attorney, Agent, or Firm* — Dicke, Billig & Czaja, PLLC

(57) ABSTRACT

One aspect relates to a method for connecting a housing of an active implantable medical device to a head part, whereby an uncured joining agent that is arranged, at least in part, between the housing and the head part is transitioned into a cured joining agent to attain a firmly bonded connection. In one embodiment, the uncured joining agent includes monomers of a (meth)acrylic acid alkyl ester, and the cured joining agent includes at least one polymer of the (meth)acrylic acid alkyl ester.

18 Claims, 6 Drawing Sheets

ACTIVE IMPLANTABLE DEVICE

CROSS-REFERENCE TO RELATED APPLICATIONS

This Utility Patent Application claims priority to German Patent Application No. DE 10 2010 021 381.0, filed on May 25, 2010 and to German Patent Application No. DE 10 2011 016 702.1, filed on Apr. 11, 2011, which are both incorporated herein by reference.

BACKGROUND

One aspect relates to a method for connecting a housing of an active implantable medical device to a head part.

In many examples, the housing and the head part of active implantable devices are connected directly to each other. In this approach to a solution, at least one head part made of epoxy resin is connected directly to the titanium housing in the course of the manufacturing. In this variant, the epoxy resin is cast in a mould and contacts the roughened-surface titanium housing while it is curing. Alternatively, the head part can be pre-fabricated and then plugged onto the housing, whereby the exact positioning is effected, for example, through metal pins on the housing. In addition, the connecting site is glued together with silicone. As is evident in particular from "HeartRhythm" 2010, 7(5), 701-704, it has proven to be disadvantageous that the known connections between housing and head part are not sealed tight with respect to body fluids and the connecting methods employed are very time-consuming.

For these and other reasons there is a need for the present invention.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

Further measures and advantages are evident from the claims, the description provided hereinafter, and the drawings. Aspects are illustrated through several exemplary embodiments in the drawings. In the figures:

DETAILED DESCRIPTION

Figure 1:
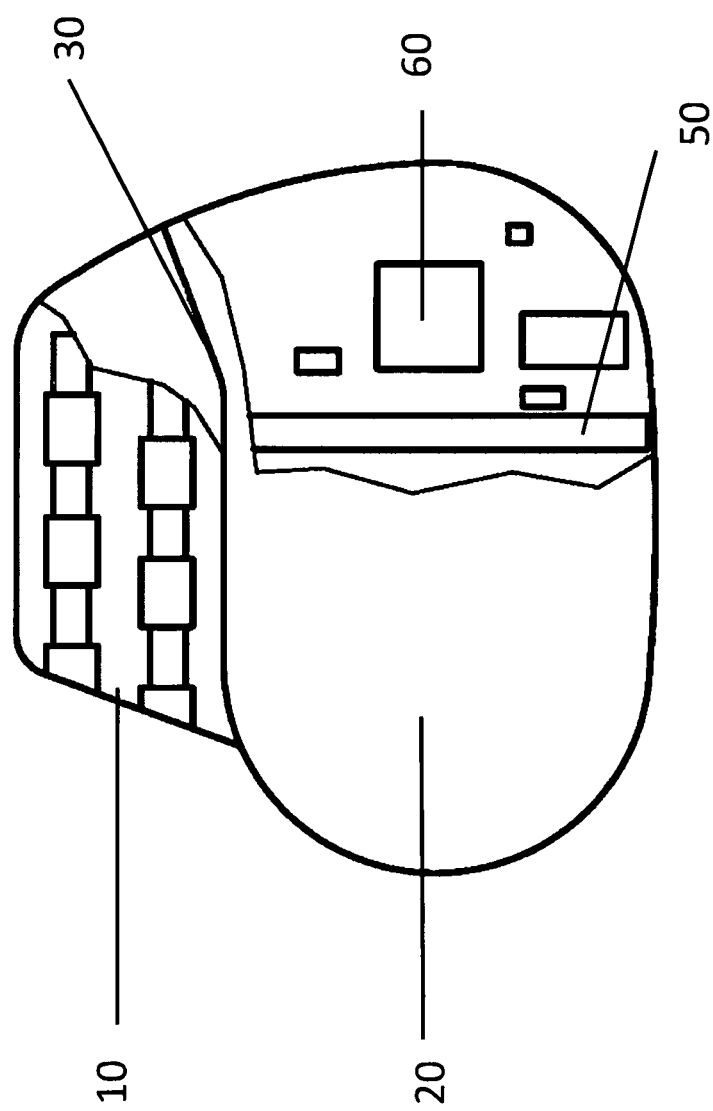
FIG. 1 illustrates an active implantable device.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

A method for the manufacture of an active implantable medical device having the features of claim 1 is proposed in order to meet said object. Moreover, an active implantable medical device is proposed to meet said object. Features and details that are described in relation to the active implantable medical device shall also apply with regard to the method, and vice versa.

One aspect is a method for connecting a housing of an active implantable medical device to a head part, whereby an uncured joining agent that is arranged, at least in part, between the housing and the head part is transitioned into a cured joining agent to attain a firmly bonded connection, whereby
  the uncured joining agent includes monomers of a (meth) acrylic acid alkyl ester, and
  the cured joining agent includes at least one polymer of the (meth)acrylic acid alkyl ester.

The use of the joining agent according to one embodiment allows a connection, which is sealed tight for media, that is, a sufficient tightness of the connection with respect to the ingress of liquids in the scope of the intended use—at the transition sites between the head part and the housing, to be attained. The cured joining agent includes at least one type of (meth)acrylic acid alkyl ester. Accordingly, one embodiment includes the joining agent to be based on a two-component mixture—aside from other admixtures—in which one component is at least one polymer of a (meth)acrylic acid alkyl ester. Polymers of this type can be considered to be starting material for two-component adhesives and/or two-component cements that are to be used within embodiments to attain a firmly bonded connection between the housing and the at least one head part.

Due to their utilization, the biocompatibility of implantable medical devices is usually one of the foremost requirements. The implantable medical device proposed herein according to one embodiment, can be inserted, in particular, into a body of a human or animal user, in particular of a patient. As a result, the implantable medical device is usually exposed to a fluid of a body tissue of the body. Accordingly, it is usually of significance for the joining agent to be biocompatible.

As a general rule, the term, implantable medical device, includes any device that is set up to carry out at least one medical function and which can be inserted into a body tissue of a human or animal user. As a general rule, the medical function can include any function selected from the group consisting of a therapeutic function, a diagnostic function, and a surgical function. In particular, the medical function can include at least one actuator function, in which an actuator is used to exert at least one stimulus on the body tissue, in particular an electrical stimulus.

As a general rule, the term, active implantable medical device—also called AIMD—include all implantable medical devices that can guide electrical signals from a hermetically sealed housing to a part of the body tissue of the user and/or receive electrical signals from a part of the body tissue of the user. Accordingly, the term, active implantable medical device, includes, in particular, cardiac pacemakers, cochlea implants, implantable cardioverters/defibrillators, nerve, brain, organ or muscle stimulators as well as implantable monitoring devices, hearing aids, retinal implants, muscle stimulators, implantable drug pumps, artificial hearts, bone growth stimulators, prostate implants, stomach implants or the like.

The implantable medical device, for example, the active implantable medical device, can usually include, for example, at least one housing, for example at least one hermetically sealed housing. The housing can in one example enclose at least one electronics unit, for example a triggering and/or analytical electronics unit of the implantable medical device.

In the scope of one embodiment, a housing of an implantable medical device shall be understood to be an element that encloses, at least in part, at least one functional element of the implantable medical device that is set up to perform the at least one medical function or promotes the medical function. In one embodiment, the housing includes at least one internal space that takes up the functional element fully or in part. In one embodiment, the housing can be set up to provide mechanical protection to the functional element from stresses occurring during operation and/or handling, and/or protection to the functional element from influences of its surroundings such as, for example, influences of a body fluid. The housing can, for example, border and/or close the implantable medical device with respect to the outside.

In known medical devices, also called electrical therapy devices, it is common to provide a hermetically sealed metal housing, which includes, on one side, a head part, also called header or connecting body, that carries connection sockets—or contact sockets—for connection of leads, also called electrode leads. The connection sockets include electrical contacts that serve to electrically connect the leads to the control electronics unit on the inside of the housing of the medical device. Usually, an electrical bushing is provided in any place, in which the electrical connection enters the housing of the medical device, and the electrical bushing is inserted into a corresponding opening of the housing in a hermetically sealing manner.

In one embodiment, a head part—also called header or connecting head—shall generally be understood to be an element that serves to take up and provide electrical contact for electrode lead connectors. Said electrode lead connectors are situated at the proximal end of an electrode lead, also called lead, which, in its implanted condition, reaches, through its distal end, to a body site to be stimulated, for example a heart chamber, and includes stimulation and/or defibrillation electrodes in said location. The electrodes are electrically connected to corresponding contacts of the electrode lead connector. For further connection to an electronics unit on the inside of the housing, the head part includes contact sockets for contacting which act in concert with corresponding electrical contact elements of the electrode lead. The electrical contact elements of the head part in turn are electrically connected to the electronics unit on the inside of the housing. This is effected regularly through so-called bushings that are arranged in the interface between housing and head part. The head part, for example, can project from the housing and can be arranged fully or in part on the housing or in the external space, but, as a general rule, it can just as well project into the internal space such that the plug connection is accessible, for example, through an opening in the housing. The head part in one embodiment includes a plastic material such as, for example, a silicone and/or epoxy resin and/or a polyurethane.

The term, "polymer of a (meth)acrylic acid alkyl ester", shall be understood to mean a type of polymer of the (meth) acrylic acid alkyl ester. The cured joining agent itself is made up of a plurality of polymer chains of at least one type of the possible polymers of a (meth)acrylic acid alkyl ester. In one embodiment, the cured joining agent shall include at least one polymer of a (meth)acrylic acid alkyl ester. In this context, the alkyl group of the ester shall denote a part of a molecule that consists of carbon and hydrogen atoms bonded to each other, which is the common definition in chemistry. Accordingly, the (meth)acrylic acid alkyl ester according to one embodiment can be at least one from the following group: (meth)acrylic acid methylester, (meth)acrylic acid ethylester, (meth)acrylic acid propylester, (meth)acrylic acid butylester or (meth)acrylic acid pentylester. The number of C-atoms of the alkyl group in one embodiment is from 1 to 10, in one embodiment 1 to 6, in one embodiment 1 to 4. This concerns branched or non-branched, in one embodiment preferably non-branched, as well as saturated or unsaturated, in one embodiment preferably saturated hydrocarbons. The term, "(meth)acrylic acid alkyl ester", is to clarify that the cured and/or uncured joining agent according to in one embodiment can include methacrylic acid esters and/or acrylic acid esters according to the scope of in one embodiment. In the scope of one embodiment, the term, polymer, is to include both homopolymers, that is, polymers that are fully made up of just one monomeric compound, and copolymers, that is, polymers that consist of two or more different monomer units.

In the scope of one embodiment, the term, "chemical bond", describes a physico-chemical phenomenon through which two or more atoms or ions are firmly bonded to each other to form chemical compounds. This is based on it being energetically more favorable for most atoms or ions to be bonded to suitable bonding partners rather than forming individual free particles. The bond is based either on electrostatic interactions or interactions between the electrons of two or more atoms. In many cases, both bonding mechanisms play a role.

A variant of the method according to one embodiment is characterized in that the monomers are polymerized to form polymers in the step of transitioning. Accordingly, the monomers of the uncured joining agent are converted to the polymers of the cured joining agent. A variant of the method according to one embodiment is characterized in that the uncured joining agent includes monomers of (meth)acrylic acid alkyl esters and polymerized (meth)acrylic acid alkyl esters. In the method according to one embodiment, a joining agent comprising polymers of the (meth)acrylic acid alkyl ester is used. Due to the polymerisation of the uncured joining agent, a firmly bonded connection between the housing and the head part is established. Prior to being processed between said two elements of an active implantable medical device, the uncured joining agent itself illustrates a low degree of polymerization. However, in general, the polymerization of the joining agent prior to applying it to the housing and/or head part is so minor that chain lengths of only maximally 10 are attained. The chain lengths to be attained in the scope of the polymerization to be described below are significantly larger. However, it can be stated that an refinement of the uncured joining agent according to one embodiment includes, prior to being processed, not only the monomers but also a certain fraction of polymers of the (meth)acrylic acid alkyl ester. The fraction of the polymerized (meth)acrylic acid alkyl ester relative to the uncured, that is, not yet processed—joining agent in one embodiment advantageously is less than 30% by weight, in one embodiment preferably less than 20% by weight, in one embodiment preferably less than 15% by weight, in one embodiment preferably less than 8% by weight.

A variant of the method according to one embodiment is characterized in that the uncured joining agent includes at least 70% by weight, in one embodiment preferably more than 80% by weight, in one embodiment preferably more than 85% by weight, in one embodiment even more preferably more than 92% by weight monomers of (meth)acrylic acid alkyl esters and maximally 30% by weight, in one embodiment preferably less than 20% by weight, in one embodiment preferably less than 15% by weight, in one embodiment preferably less than 8% by weight polymerized (meth)acrylic acid alkyl esters.

A variant of the method according to one embodiment is characterized in that the cured joining agent includes at least 70% by weight, in one embodiment preferably more than 80% by weight, in one embodiment preferably more than 85% by weight, in one embodiment even more preferably more than 92% by weight polymers of (meth)acrylic acid alkyl esters and maximally 30% by weight, in one embodiment preferably less than 20% by weight, in one embodiment preferably less than 15% by weight, in one embodiment preferably less than 8% by weight monomers of (meth)acrylic acid alkyl esters.

In one embodiment, it has proven to be advantageous for triggering the polymerization of the uncured joining agent that the uncured joining agent include an initiator, for example, a photoinitiator and/or a stabilizer. The purpose of the initiator is to form radicals upon external excitation, which radicals then lead to polymerization, that is, formation of a chain—of the (meth)acrylic acid alkyl ester—and thus to a transitioning of the uncured joining agent into the cured joining agent. Said polymerization of the uncured joining agent enables the firmly bonded connection between the housing and the head part to be established. The firmly bonded connection through the cured joining agent that is thus attained is advantageous in one embodiment as compared to known adhesives in that it provides increased media-tight sealing through which no liquid can diffuse any longer into the inside of the housing and/or the inside of the head part.

In the scope of one embodiment, a photoinitiator is a photoactive substance that forms radicals and triggers polymerization upon irradiation with UV light. Compounds including, for example, α-hydroketones, benzophenone, α,α-diethoxyacetophenone, 4,4-diethylaminobenzophenone, 2,2-dimethoxy-2-phenylacetophenone, 4-isopropylphenyl-2-hydroxy-2-propylketone, 1-hydroxycyclohexylphenylketone, isoamyl-p-dimethylaminobenzoate, methyl-4-dimethylaminobenzoate, methyl-o-benzoylbenzoate, benzoin, benzoin ethylether, benzoin isopropylether, benzoin isobutylether, 2-hydroxy-2-methyl-1-phenylpropan-1-one, 2-isopropylthioxanthone, dibenzosuberone, 2,4,6-trimethylbenzoyldiphenylphosphine oxide, bisacylphosphine oxide, and other compounds known to the person skilled in the art can be used in this context. Moreover, the joining agent can include at least one stabilizer. The stabilizer prevents ageing processes of the joining agent by scavenging radicals. Sterically hindered phenol derivatives, such as alkyl-substituted phenols, such as, for example, methylphenol, 4-methyl-2,6-di-tert.-butylphenol, also hydroquinone methylesters and other systems that are known to the person skilled in the art are used as stabilizers.

Another variant according to one embodiment is characterized in that the uncured joining agent is prepared by mixing a powder component, at least one liquid monomer component, and the photoinitiator, whereby the powder component includes the polymers of (meth)acrylic acid alkyl esters. Splitting the uncured joining agent according to one embodiment into a powder component including the polymers, at least one monomer component, and the photoinitiator, allows the ingredients of the uncured joining agent to be provided easily for production purposes. In addition, a stabilizer can be admixed. Inadvertent polymerization of the monomers of the (meth)acrylic acid alkyl ester is thus excluded. The manufacture of the cured joining agent according to one embodiment thus only requires mixing the powder component and the liquid monomer component. The liquid monomer component then polymerizes through appropriate reactions. Adding the liquid monomer component to the powder component advantageously generates, in one embodiment, a liquid mass that can be applied easily to the corresponding surfaces of the housing and/or head part. Only the completion of the polymerization process effects the conversion of the liquid uncured joining agent to a solid cured joining agent that provides the firmly bonded connection between housing and head part.

Polymethylmethacrylate (PMMA) bone cement is a feasible cured joining agent. Polymethylmethacrylate (PMMA) bone cements can include or consist of a liquid monomer component and a powder component. The monomer component generally contains the monomer, methylmethacrylate, and an activator (such as, for example, N,N-dimethyl-p-toluidine) dissolved therein. The powder component, also called bone cement powder, include one or more polymers that are made by polymerization, in one embodiment preferably suspension polymerization, based on methylmethacrylate and co-monomers, such as styrene, methylacrylate or similar monomers, and the initiator, for example, dibenzoylperoxide. Mixing the powder component and the monomer component, swelling of the polymers of the powder component in the methylmethacrylate generates a dough that can be shaped plastically and is the actual bone cement. Mixing the powder component and the monomer component, the activator, N,N-dimethyl-p-toluidine, reacts with dibenzoylperoxide while forming radicals. The radicals thus formed trigger the radical polymerization of the methylmethacrylate. Upon advancing polymerization of the methylmethacrylate, the viscosity of the cement dough increases until the cement dough solidifies.

Another embodiment variant is characterized in that irradiation triggers the polymerization of the uncured joining agent. Accordingly, the transitioning of the uncured joining agent to the cured joining agent is triggered by irradiation, for example, by irradiation with UV light. In this embodiment variant, supplying electromagnetic radiation leads to conversion of the monomers to polymers of the (meth)acrylic acid alkyl ester. In the scope of one embodiment, the term, "irradiation", shall be understood to mean that the uncured—or only partially cured—joining agent is irradiated with electromagnetic radiation. In this context, the wavelength spectrum from approx. 200 nm to approx. 1000 nm includes the electromagnetic radiation in the scope of one embodiment. In one embodiment, the irradiation of the uncured or just partially cured joining agent involves irradiation with a electromagnetic radiation between 250 nm and 500 nm. In order to ensure good processing properties, it has proven to be advantageous one embodiment to use the uncured joining agent in the liquid state of aggregation. This enables easy application to the corresponding surfaces of the housing and/or head part. The irradiation and the polymerization thus triggered can then trigger a change of a state of aggregation of the joining agent from liquid to solid (uncured to cured). The electromagnetic radiation, in combination with the photoinitiator, thus ensures that radicals are formed which enable the polymerization of the (meth)acrylic acid alkyl ester.

Another variant of the method according to one embodiment is characterized in that an adhesion promoter is applied to achieve a firmly bonded connection, whereby the adhesion promoter includes at least a first functional group and a second functional group. In this embodiment variant, the housing and the head part are connected to each other in a firmly bonded manner through the joining agent and the adhesion promoter, whereby the adhesion promoter includes at least a first and a second functional group. Aside from the (uncured or cured) joining agent described above, this embodiment variant utilises an adhesion promoter that is intended to further improve the connection between the housing and the head part. As illustrated above, the implantable medical device, in which the connection technology disclosed herein is to be used, often is a cardiac pacemaker. Cardiac pacemakers of this type generally include a metallic housing. The metals used for the housing—such as, for example, titanium—feature high biocompatibility and reliably prevent the ingress of liquid into the inside of the device. Plastic materials, such as, for example, silicones, are generally used for the head part. The joining agent and adhesion promoter disclosed herein allow very different materials, such as a plastic material and a metal, to be connected reliably and lastingly in a firmly bonded manner. Simultaneously, surprising measurements have illustrated that liquid cannot penetrate into said connection and thus cannot lead to a hazard for the function of the active implantable medical device. A refinement of said variant of the method is characterized in that, in at least a part of the adhesion promoter, a chemical bond is generated between the first functional group and at least one of the surfaces from the group of a contact surface of the housing or a connecting surface of the head part, and a chemical bond is generated between the second functional group and at least one polymer of the cured joining agent.

The adhesion promoter can include two functional groups. One of the two functional groups establishes a chemical bond to the housing or the head part. In contrast, the other functional group forms a chemical bond to the polymers of the (meth)acrylic acid alkyl ester of the (uncured or cured) joining agent. In this context, it has proven to be advantageous in one embodiment that the chemical bond between the contact surface of the housing and/or the connecting surface of the head part and the first functional group is established through oxygen and/or sulfur atoms. Said atoms have a bridging function and can easily establish a lasting chemical bond to metallic housing surfaces as well as to head parts made of plastic materials.

These bifunctional molecules can include the following components:

a phosphorus- or sulfur-containing functional group for adhesion to the metal surface, in one embodiment preferably including at least one of:
phosphoric acid esters or salts thereof
phosphonic acid or salts thereof
thiol or thiolates
thiol-modified triazine matrix and derivatives thereof
sulfonic acid or sulfonates
silane
a functional group for adhesion of the following component formed by a (meth)acrylate function, or
a spacer for spatial separation of the two functional groups, made of a saturated or unsaturated aliphatic hydrocarbon.

Another advantageous embodiment variant of the method is characterized in that the chemical bond between the contact surface of the housing and/or the connecting surface of the head part and the first functional group is established by means of thiol-modified triazine matrices and/or a phosphate group. The chemical compounds mentioned above allow for reliable establishment of a firmly bonded connection featuring high shear force. Moreover, they are resistant to body fluids and easy to process.

The purpose of the second functional group of the adhesion promoter is to engage in a chemical bond to at least one polymer of the (uncured or cured) joining agent. In order to implement said bond, the second functional group can include at least one unsaturated hydrocarbon group. Hydrocarbon groups of this type engage rapidly and reliably in lasting chemical bonds to the polymers of the (meth)acrylic acid alkyl ester and afford a stable, lasting, and media-tight connection between the housing and/or head part and the cured or not yet completely cured joining agent. In a further refinement, the second functional group can be an alkylacrylate, for example a methacrylate, or an acrylate. Comparative tests have illustrated that it is advantageous in one embodiment for the adhesion promoter to include the following combination of first and second functional group:

the first functional group is a triazine matrix and the second functional group is an acrylate or the first functional group is a phosphate group and the second functional group is a methacrylate.

Adhesion promoters including the specified combination of first and second functional group allowed firmly bonded connections between the housing and the head part with the highest shear forces to be established.

Another embodiment variant is characterized in that the initiator of the uncured joining agent and/or an initiator of the adhesion promoter form radicals upon irradiation and trigger a polymerization of the monomers of the (meth)acrylic acid alkyl ester. Depending on the refinement, the initiator triggering the polymerization can therefore be integrated in the uncured joining agent, in the adhesion promoter or in both. The type of application, in which the initiator is to be introduced, depends essentially on the state of aggregation of the individual component and/or the processing conditions of the joining agent and/or adhesion promoter.

In an advantageous refinement, the uncured and/or cured joining agent acts in concert with the adhesion promoter. A durable firmly bonded connection between the head part and the housing is attained through the concerted action of the adhesion promoter and, for example, the cured joining agent. The adhesion promoter includes bifunctional molecules which each form chemical bonds to the metal surface through their functional groups (phosphoric acid esters, thiol groups). Said functional groups are connected to an acrylate or methacrylate group each through an alkyl chain or a triazine matrix with alkyl chain. These can polymerize into the polymer of the second component, that is, the joining agent. The cured joining agent reinforces the adhesive bond through very good wetting of the metal surface and—due to the low viscosity—good hooking into micro-fissures or the like. Micro-fissures of this type can be introduced into the housing and/or head part, for example, by sand-blasting.

The purpose of the cured joining agent and/or adhesion promoter is to connect the housing and the at least one head part. In one embodiment, the joining agent and/or adhesion promoter advantageously joins—as defined according to DIN 8593—the housing and the at least one head part. It is preferred in one embodiment that the cured joining agent and/or the adhesion promoter glues the housing and the at least one head part together. Forces that may be acting are transferred via the effective surfaces of the connection. In this context, the cured joining agent and/or the adhesion promoter acting as adhesive adheres to the surface of the part to be joined through physical (rarely through chemical) interactions.

Another variant of the method according to one advantageous embodiment is characterized in that the connecting includes the following steps:

applying the uncured joining agent (30, 30', 30") to at least one surface from the group of contact surface of the housing (20) and connecting surface of the head part (10);

placing the contact surface and the connecting surface on top of each other, at least partly; and at least partial transitioning of the uncured joining agent to the cured joining agent (30, 30', 30").

In order to attain a desired firmly bonded connection between the housing and the head part, it is necessary to apply the uncured joining agent to at least one of said two surfaces of the head part and housing that are to be connected to each other. In the scope of one embodiment, the term, contact surface, shall refer to the region of the housing that is arranged in the immediate geometrical vicinity of the head part and through which a firmly bonded connection to the head part is to be established. The corresponding surface of the head part is referred to as connecting surface. In one embodiment, the contact surface and the connecting surface are advantageously provided to be complementary to each other.

Another embodiment variant is characterized in that the transitioning of the uncured joining agent to the cured joining agent is triggered by an irradiation, for example by an irradiation with UV light.

Another variant of the method according to one embodiment is characterized in that the method includes the following step at least prior to applying the uncured joining agent (30,30',30"):

applying the adhesion promoter (40) to at least one of the surfaces from the group of contact surface of the housing (20) and connecting surface of the head part (10).

The procedural steps listed above are supplemented through the present step in that not only the uncured joining agent, but also the adhesion promoter, is applied to at least one of the two surfaces to be contacted—contact surface and connecting surface. The comparative measurements have illustrated in one embodiment that it is advantageous to apply the adhesion promoter to the contact surface and/or connecting surface prior to applying the uncured joining agent. Said embodiment variant can be supplemented in that, prior to the placing on top of each other, at least one from the group of uncured joining agent and adhesion promoter is irradiated, for example is irradiated with UV light. The irradiation triggers a polymerization of the monomers of the (meth)acrylic acid alkyl ester. As has been explained, said polymerization results in solidification of the uncured joining agent and thus in a firmly bonded connection between the housing and the head part. However, said polymerization is a process that takes a certain period of time during which the two components of the implantable medical device can be placed on top of each other in the scope of one embodiment. It has proven to be advantageous in one embodiment to irradiate after the placing on top of each other, at least one from the group of joining agent and adhesion promoter, for example to irradiate with UV light. Said irradiation can be utilized as a supplementary irradiation in order to intensify and/or further support the polymerization reaction.

Another variant of the method according to one embodiment is characterized in that the contact surface of the housing or the connecting surface of the head part is cleaned prior to applying the uncured joining agent and/or prior to applying the adhesion promoter. Said cleaning ensures that the first functional group of the adhesion promoter and/or the uncured joining agent form chemical bonds to the contact surface or the connecting surface, and that said formation of chemical bonds is not made more difficult by contamination.

In an advantageous example, the Ti surface of a housing—also called pacemaker housing—as well as the polymer surface of the head part are cleaned and simultaneously roughened by sand-blasting (for example, Ti: 110 μm Al2O3 blasting sand, 3 bar compressed air, plastic material: 50 μm Al2O3 blasting sand, 2 bar compressed air) (approx. 10 sec). Subsequently, the surfaces are cleaned with distilled water and blown dry with oil-free compressed air. An acetone-based adhesion promoter is then applied in timely fashion in order to prevent contamination of the surfaces. The joining agent is applied after the solvent is evaporated. The joining agent includes a PMMA/MMA mixture as well as further multifunctional (meth)acrylate monomers, photoinitiators, and stabilizers. Said second component is then also applied to the surface of the plastic material.

In the scope of the method, the two surfaces can either be
1. irradiated separately and then joined by pressing them together and/or
2. glued to each other by pressing them together and subsequently irradiating them jointly.

In this context, the irradiation is carried out using a light source matched to the photoinitiators, for example, a UV or flash discharge lamp for a period of 1-5 minutes, advantageously in one embodiment for 2-4 min.

The pre-treatment by sand-blasting described above can be advantageous for the adhesive connection of the joining agent and/or adhesion promoter to the two components. However, a process including a simplified/shortened pre-treatment or complete absence of a pre-treatment shall also be included in the subject matter of one embodiment.

Another advantageous exemplary embodiment of the method according to the one embodiment includes the following procedural steps:

1) Sand-blasting the surface of the housing (advantageously with blasting sand 110 μm, 3 bar). Subsequent cleaning with distilled water and drying with oil-free compressed air.

2) Applying an adhesion promoter (for example, Signum bond I made by Heraeus Kulzer) to the surface of the housing.

3) Applying the joining agent (for example, Signum zirconia bond II made by Heraeus Kulzer) to the surface of the housing.

4) Irradiating the surface of the housing for 90 sec with a light polymerization unit (for example, Heraflash made by Heraeus Kulzer).

5) Sand-blasting the plastic surface of the head part (advantageously with blasting sand 50 μm, 2 bar). Subsequent cleaning with distilled water and drying with oil-free compressed air.

6) Applying the joining agent (for example, Signum zirconia bond II made by Heraeus Kulzer) to the surface of the head part.

7) Irradiating the surface of the head part for 90 sec with a light polymerization unit (for example, Heraflash made by Heraeus Kulzer).

8) Joining and pressing together both components.

9) Irradiating the joining agent at the connecting site for another 180 sec with a light polymerization unit (for example, Heraflash made by Heraeus Kulzer).

Another variant of the method according to one embodiment is characterized in that the adhesion promoter and/or the uncured joining agent has a viscosity between 10 and 30 MPas, in one embodiment 15-20 MPas, at 23° C. and a shear rate of 100 l/sec when it is applied to the contact surface of the housing and/or the connecting surface of the head part. Utilizing an adhesion promoter and/or uncured joining agent of appropriate viscosity ensures that the contact surface or the connecting surface is wetted evenly. No individual droplets or non-wetted surfaces are formed on the connecting surface/contact surface, which are not wetted by the adhesion promoter and/or uncured joining agent. Thus, after firmly bonded joining of the housing and head part—for example after transitioning the uncured joining agent into the cured joining agent—no gaps or hollow spaces are formed through which liquids might penetrate into the adhesive bond between housing and head part.

The results of tests based on ISO 10477 illustrated a shear adhesive strength between 20 MPa and 30 MPa, in one embodiment of more than 25 MPa, in part of more than 30 MPa, in one embodiment of up to 36 MPa for the bonds between housing and head part provided the joining agent according to one embodiment and the adhesion promoter according to one embodiment were utilized. The minimal requirement for the cured adhesion promoter is 5 MPa if one works without macromechanical retention—which is the case here.

The object specified above is also met by an active implantable medical device having a housing and a head part, whereby the head part covers at least part of the housing, and the housing and the head part are connected to each in a firmly bonded manner through a cured joining agent. In the scope of one embodiment, the cured joining agent includes at least one polymer of a (meth)acrylic acid alkyl ester.

Utilizing a cured joining agent as provided according to one embodiment ensures that the implantable device according to the one embodiment includes a hermetically sealed connection between housing and head part through which no body fluids can penetrate into the implantable device or through which no inadvertently leaking liquids from an electronics unit on the inside of the housing might find their way into the body of a patient.

An advantageous refinement of the implantable medical device described herein is characterized in that the housing surrounds a stimulator at least partly, and the head part covers at least parts of a bushing in the housing. As illustrated, the implantable device primarily is a cardiac pacemaker or defibrillator. The inside of the housing accommodates the components needed to form a stimulator that generates electrical pulses through which, for example, a heart can be stimulated. The electrical pulses generated by the stimulator on the inside of the housing are conducted from the housing through an electrically conductive bushing. The head part generally serves as connector for a lead that conducts the electrical pulse from the implantable device to the electrode on the heart muscle. It has proven, in one embodiment, to be advantageous to have the head cover at least parts of said bushing that are arranged in an opening of the housing.

Another advantageous refinement is characterized in that the housing and the head part are connected to each other in a firmly bonded manner through the cured joining agent and an adhesion promoter, in that the adhesion promoter includes at least one type of bifunctional molecules, and in that, at least in part of the adhesion promoter,
 a chemical bond exists between the first functional group and at least one of the surfaces consisting of a contact surface of the housing or a connecting surface of the head part, and
 a chemical bond exists between the second functional group and at least one polymer of the cured joining agent.

Some advantages of the adhesion promoter have been discussed above. In this context, advantages and features that have been disclosed with regard to the method according to embodiments shall apply equally to the implantable device according to embodiments.

Another embodiment variant is characterized in that the uncured and/or cured joining agent and/or the adhesion promoter includes at least one initiator, for example one photo-initiator, whereby it is preferred in one embodiment that the photoinitiator forms radicals upon irradiation with UV light and triggers a polymerization. Integrating the initiator into the uncured joining agent and/or the adhesion promoter ensures even and homogeneous polymerization of the above-mentioned substances and thus ensures that the housing and the head part engage in a firmly bonded connection that has high combined tension and shear resistance.

It is also advantageous in one embodiment that the bifunctional molecule of the adhesion promoter includes a spacer for spatial separation of the first and the second functional group. The first and the second functional group of the adhesion promoter serve different purposes. In order to ensure that the adhesion promoter that is connected, on the one hand, to the housing or the head part projects sufficiently deep into the polymerized (meth)acrylic acid alkyl ester chains, it is advantageous in one embodiment to attain some spatial separation between the two functional groups. This is the task assumed by the spacer. In one embodiment it is advantageous for the spacer to include saturated hydrocarbons, for example, an alkyl chain and/or a triazine matrix with alkyl chains. This allows the two functional groups to be spatially separated in a clean manner, to bridge substantial spatial distances, and to ensure at the same time that a chemical bond with high combined tension and shear resistance is formed a once the functional groups are connected to their respective connection partners. It has proven to be advantageous in one embodiment for attaining the desired liquid-proof, pore-free, and firmly bonded connection between the housing and the head part that the first functional group includes thiol-modified triazine matrices and/or phosphate groups and/or the second functional group includes alkylacrylate, for example methacrylate, or acrylate. Utilizing single or multiple combinations of the specified features allows to generate an active implantable device with a firmly bonded connection between the housing and the head part that has a combined tension and shear resistance between 20 MPa and 40 MPa, for example between 30 MPa and 40 MPa.

The implantable device described herein is connected in a firmly bonded manner through a cured joining agent that includes a polymer of a (meth)acrylic acid alkyl ester. In this context, it has proven to be advantageous that the housing or part of the housing is made of titanium or a titanium-containing alloy. Utilizing the joining agent described herein allows a housing that is provided as described to be connected to a head part that is characterized in that the head part or parts of the head part Is/are made of a polyurethane or polyurethane derivative.

Another advantageous refinement of the implantable device is characterized in that the head part is permeable for an electromagnetic radiation for excitation of the photoinitiators of the adhesion promoter, for example in that the head part is transparent for an electromagnetic radiation within a wavelength range from 300 nm to 600 nm, in one embodiment preferably, in that the degree of transmission of the head part for electromagnetic radiation in the wavelength range between 350 nm and 440 nm is better than 40%. The refinement of the head part thus described allows homogeneous and even irradiation of the photoinitiator by the electromagnetic radiation to be attained. An even reaction of the photoinitiator and thus an even polymerization of the (meth)acrylic acid alkyl ester are thus triggered. This prevents individual regions of the uncured joining agent from polymerizing insufficiently. A head part having the features described herein is of special significance, for example when the components of the implantable device to be connected are subject to high combined tension and shear forces or if particularly large quantities of the uncured joining agent are to polymerize evenly. It has proven to be advantageous with most implantable devices that a distance between the housing and the head part arising from the joining agent is maximally 500 µm, in one embodiment between 400 µm and 100 µm.

It has proven to be advantageous in one embodiment that the implantable device described herein is characterized in that the housing and the head part are connected through one of the methods described herein.

What is also claimed is the use of a polymer of a (meth) acrylic acid alkyl ester for connecting a housing and a head part of an active implantable device in a firmly bonded manner. What is also claimed is the use of a polymer of a (meth) acrylic acid alkyl ester and of a bifunctional molecule to connect a housing and a head part of an active implantable device in a firmly bonded manner. Moreover, what is also claimed is the use of a mixture of a polymer of a (meth)acrylic acid alkyl ester and of a bifunctional molecule to connect a housing and a head part of an active implantable device in a firmly bonded manner, whereby, in at least a part of the bifunctional molecules,
 a first functional group of the bifunctional molecule engages in a chemical bond to the housing or head part, and
 a second functional group of the bifunctional molecule engages in a chemical bond to the polymer of the (meth) acrylic acid alkyl ester.

An advantageous refinement of the active implantable device is characterized in that the housing and the head part are glued together by means of a (meth)acrylate-based adhesive. Thus results an active implantable device with a connection between housing and head part that is tight and durable with respect to body fluids and water.

An advantageous refinement of the active implantable device is characterized in that the housing and the head part are connected by means of a 2-component system. The first component—the adhesion promoter—includes bifunctional molecules having phosphoric acid and (meth)acrylate groups. The adhesion promoter can preferably in one embodiment also include bifunctional molecules having thiol and (meth)acrylate groups.

The second component—the joining agent—includes a methylmethacrylate, PMMA and/or another multi-functional (meth)acrylate. It is advantageous in one embodiment for the joining agent to be light-curing.

An advantageous embodiment of the active implantable device is characterized in that the housing is made of titanium and/or the head part is made of a polyurethane or polyurethane derivative (for example tecothane). An advantageous embodiment of the active implantable device is characterized in that the head part is made of a polymer that is translucent in the range of wavelengths required for excitation of the photoinitiators.

An advantageous embodiment of the active implantable device is characterized in that an adhesive joint made up of joining agent and adhesion promoter is maximally 500 µm, in one embodiment between 400 µm and 100 µm, in thickness. The thickness of the connection, according to one advantageous embodiment, between housing and head part is such that no thermal post-cure is required.

FIG. 1 illustrates for exemplary purposes an implantable device 100, such as, for example a cardiac pacemaker, that has a head part 10 integrated into its metallic housing 20. The head part 10 is connected to the housing 20 of the implantable device 100 in a media-tight manner, in one embodiment advantageously so through utilizing a joining agent 30 that has been cured according to one embodiment. An electronic circuit 60, for example, that is operated through a battery 50 can be arranged in the housing 20. A conducting coil—not illustrated in the drawing—projects into the head part 10 and is connected to a stimulation electrode. Stimulation electrodes of this type are used, for example, in heart muscles to allow signals of the cardiac pacemaker to be conducted to the muscle. A joining agent 30, according to one embodiment, and/or an adhesion promoter 40, effect a firmly bonded connection between the housing 20 and the head part 10.

Figure 2B:
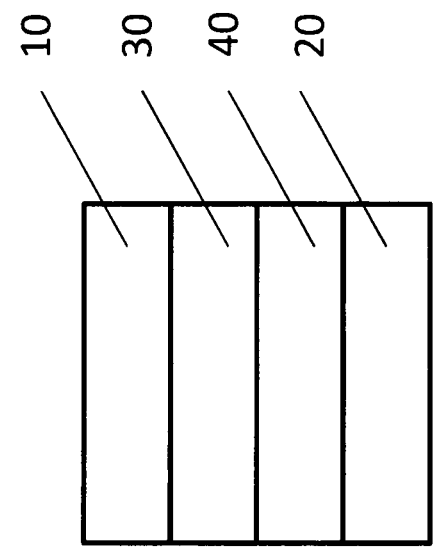
FIGS. 2a and 2b illustrate a drawing of a section through the active implantable device.
Figure 2A:
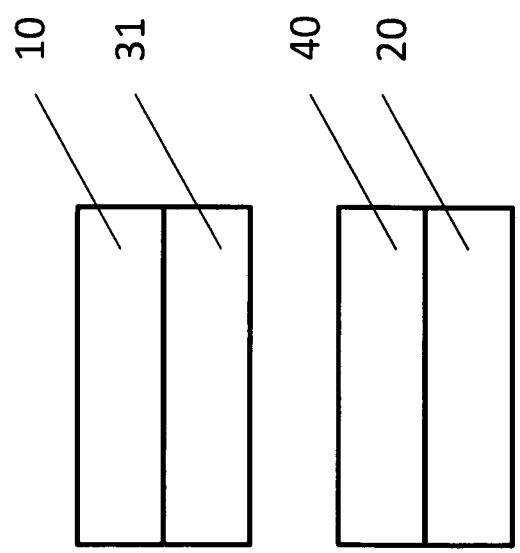

FIGS. 2a and 2b illustrate the connection according to one embodiment between the parts of the implantable device 100. The housing 20 and head part 10 are still separate in FIG. 2a. An adhesion promoter 40 is applied to the housing 20. Said adhesion promoter 40 includes bifunctional molecules. The uncured joining agent 31 is applied to the head part. Subsequently, the housing 20 is connected to the head part 10 as illustrated in the drawing of a section illustrated in FIG. 2b.

An advantageous embodiment variant of the method according to one embodiment is characterized in that the monomers are polymerized to form polymers in the step of transitioning. Accordingly, the monomers of the uncured joining agent are converted to the polymers of the cured joining agent.

Accordingly, the connection between the housing 20 and the head part 10 can be provided through the following sequence of steps:
 1.) Preparatory steps:
 sand-blasting the surface of the housing 20;
 cleaning the housing 20 with distilled water and drying it with oil-free compressed air;
 applying the adhesion promoter 40 to the surface of the housing 20;
 applying the uncured joining agent 31 to the surface of the housing 20;
 sand-blasting the surface of the head part 10;
 cleaning the surface of the head part 10 with distilled water and drying it with oil-free compressed air;
 applying the uncured joining agent 31 to the surface of the head part 10;
 2.) Connecting steps:
 a) irradiating the housing 20 and the head part 10 prior to joining them:

irradiating the surface of the housing 20 for approximately 90 sec with a light polymerization device;
irradiating the surface of the head part 10 for approximately 90 sec with the light polymerization device;
or
b) irradiating the housing 20 and the head part 10 only after joining them;
or
c) irradiating one of the housing 20 or head part 10 before and one after joining them:
irradiating the surface of the housing 20 or the surface of the head part 10 for 90 sec with a light polymerization device;
3.) Final joining and irradiation:
joining the housing 20 and the head part 10 and pressing them together; and
irradiating the uncured joining agent 31 at a connecting site of the head part 10 and the housing 20 with the light polymerization device such that the cured joining agent 30 is generated.

Figure 3:
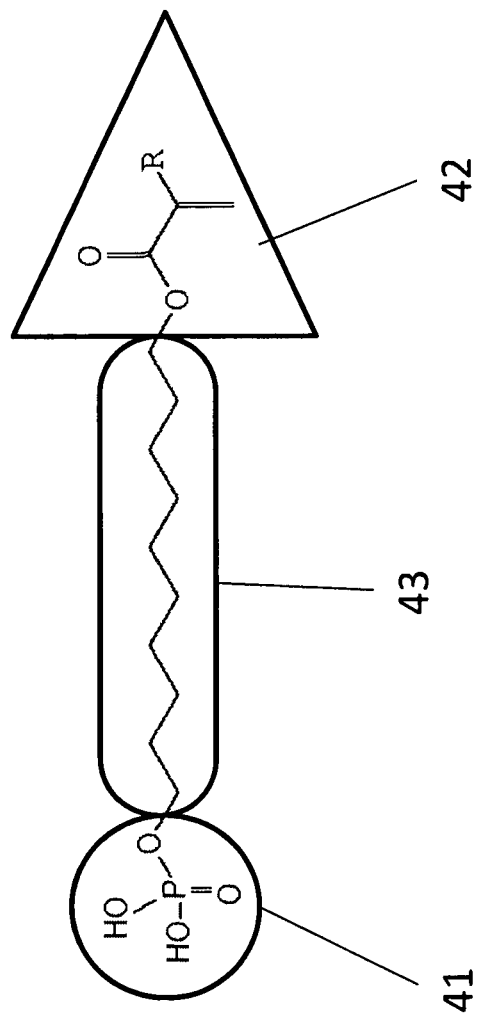
FIG. 3 illustrates a schematic structure of a bifunctional molecule of an adhesion promoter.

FIG. 3 illustrates the schematic structure of a bifunctional molecule that is a component of the adhesion promoter 40. The bifunctional molecule includes two functional groups 41,42 which are connected to each other through a spacer 43. The first functional group 41 is illustrated schematically as phosphoric acid group. However, it can just as well be made up of other phosphorus- and/or sulfur-containing functional groups. The spacer 43 is illustrated in exemplary fashion as aliphatic hydrocarbon chain with 10 CH2 units. This is not to be understood as a limitation, though. Hydrocarbon chains with 2, 4 or 6 or a larger number of CH2 units are feasible just as well. The second functional group 42 is made up of an acrylate (R=H) or an alkylacrylate, such as, for example, methacrylate (R=CH3).

Figure 4:
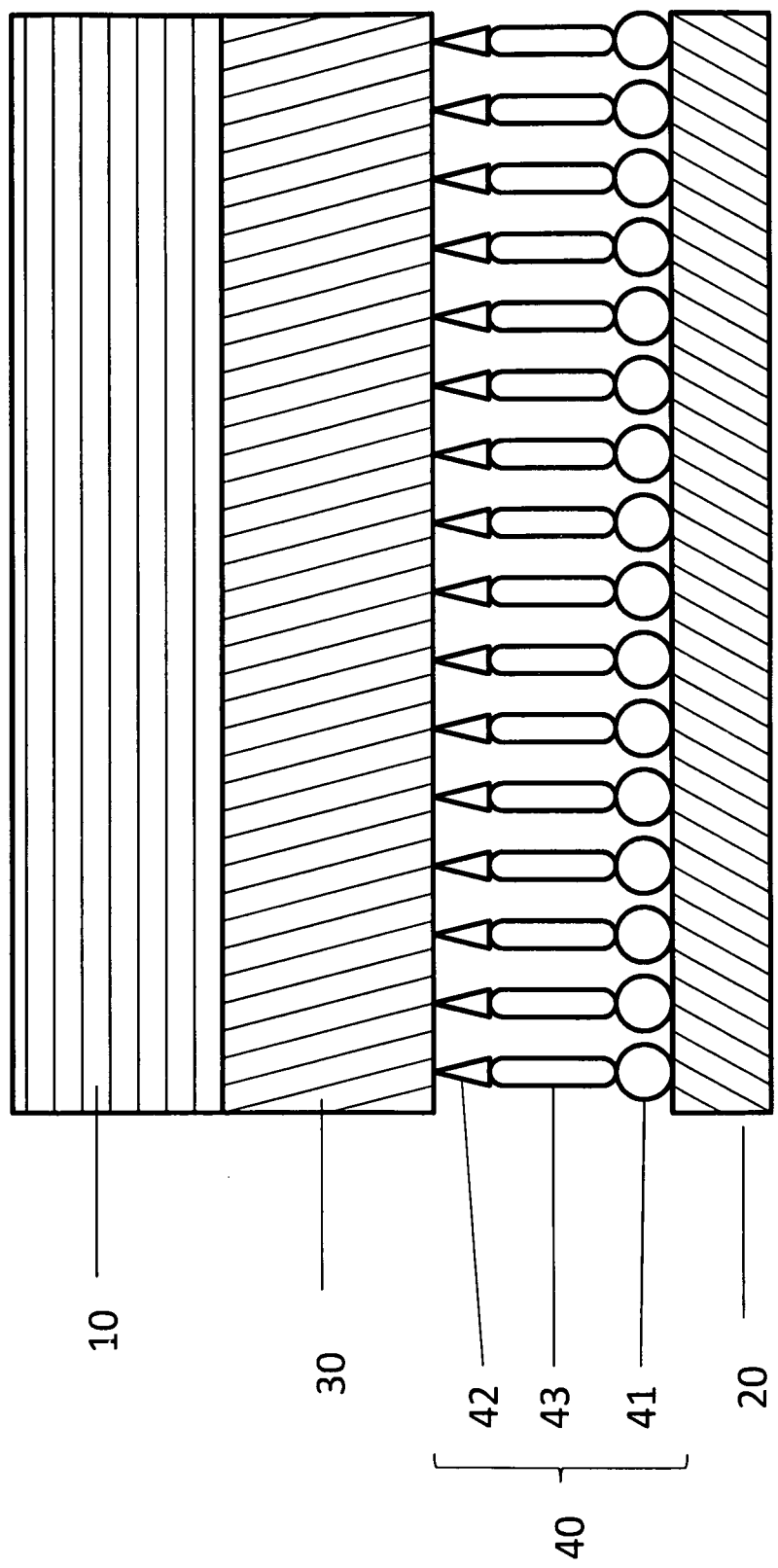
FIG. 4 illustrates another drawing of a section through the active implantable device.

The arrangement of the adhesion promoter 40 between the housing 20 and the joining agent 30 is illustrated in FIG. 4, which is analogous to FIG. 2b in all other respects. Both FIG. 4 and FIG. 5 to be described below illustrate the arrangement of the two groups 41,42 of the bifunctional molecule, which is a component of the adhesion promoter 40.

Figure 5:
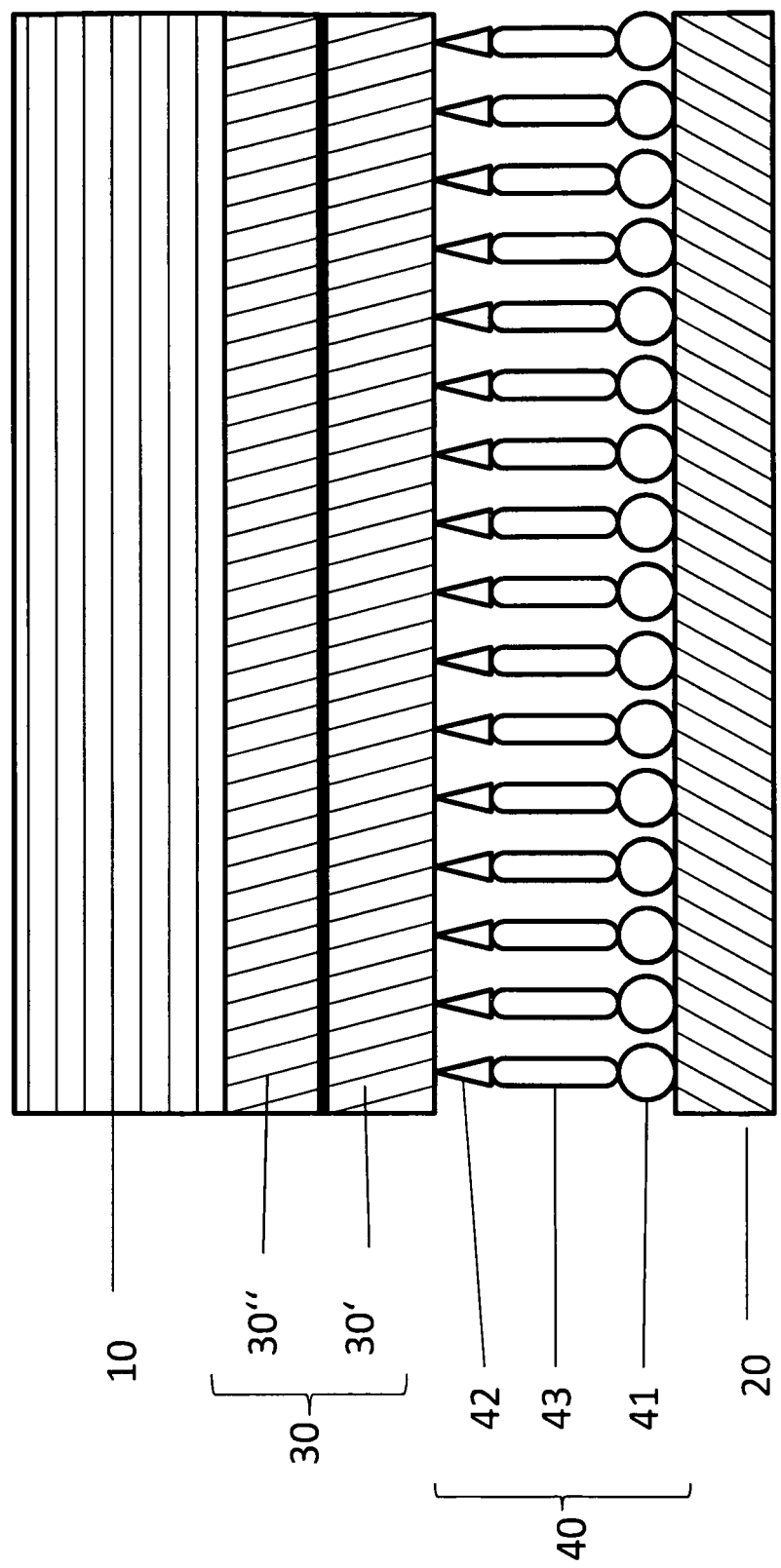
FIG. 5 illustrates another drawing of a section through the active implantable device.

The arrangement of the adhesion promoter 40 between the housing 20 and the cured joining agent is illustrated in FIG. 5, which is analogous to FIGS. 2b and/or 3 in all other respects. However, a schematic sub-division of the joining agent 30 is recognizable herein. Said uncured joining agent was applied to both the housing 20 and the head part 10 prior to assembling the implantable device 100. Accordingly, the cured joining agent 30 is subdivided into a fraction 30' that is arranged on the adhesion promoter 40 on the housing 20, and a fraction 30" that is arranged on the head part. Joining the implantable device 100, said two fractions 30', 30" combine to form the joining agent 30, which is joint initially uncured and later irradiation-cured, and enable the firmly bonded connection.

Figure 6:
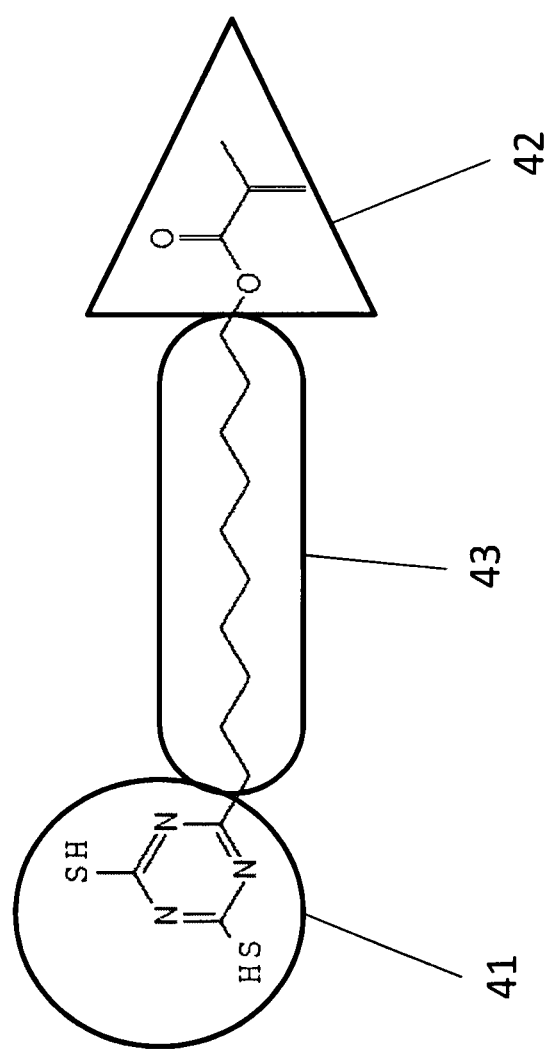
FIG. 6 illustrates a schematic structure of another bifunctional molecule of the adhesion promoter.

FIG. 6 illustrates another schematic structure of a bifunctional molecule that is a component of the adhesion promoter 40. The arrangement of the functional groups 41,42 and spacer 43 is analogous to FIG. 3. In contrast to FIG. 3, the first functional group—also called functional group 1—includes a thiol-modified triazine derivative.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A method for connecting a housing of an active implantable medical device to a head part of the active implantable medical device,
whereby the head part is configured to provide electrical contact for lead connectors to the active implantable medical device and the housing is configured to hermetically enclose at least one functional element of the medical device,
whereby an uncured joining agent that is arranged, at least in part, between the housing and the head part is transitioned into a cured joining agent to attain a firmly bonded connection between the housing and the head part,
whereby
the uncured joining agent comprises monomers of a (meth)acrylic acid alkyl ester, and
the cured joining agent comprises at least one polymer of the (meth)acrylic acid alkyl ester;
characterized in that the uncured joining agent comprises at least 70% by weight (meth)acrylic acid alkyl ester monomers and maximally 30% by weight polymerized (meth)acrylic acid alkyl esters and in that the uncured joining agent comprises a stabiliser and/or an initiator.

2. The method according to claim 1, characterized in that the cured joining agent comprises at least 70% by weight polymer of (meth)acrylic acid alkyl esters and maximally 30% by weight (meth)acrylic acid alkyl ester monomers.

3. The method according to claim 1, characterized in that the uncured joining agent comprises a photoinitiator.

4. The method according to claim 1, characterized in that the method comprises the following steps:
(A) applying the uncured joining agent to at least one surface from the group of contact surface of the housing and connecting surface of the head part;
(B) placing the contact surface and the connecting surface on top of each other, at least partly; and
(C) transitioning the uncured joining agent into the cured joining agent, at least partly.

5. The method according to claim 4, characterized in that the step of transitioning comprises an irradiation.

6. The method according to claim 5, characterized in that the step of transitioning comprises an irradiation with UV light.

7. The method according to claim 4, characterized in that the method comprises the following step at least prior to applying the uncured joining agent:
applying an adhesion promoter to at least one of the surfaces from the group of contact surface of the housing and connecting surface of the head part.

8. A method for connecting a housing of an active implantable medical device to a head part of the active implantable medical device,
whereby the head part is configured to provide electrical contact for lead connectors to the active implantable medical device and the housing is configured to hermetically enclose at least one functional element of the medical device,
whereby an uncured joining agent that is arranged, at least in part, between the housing and the head part is transitioned into a cured joining agent to attain a firmly bonded connection between the housing and the head part,
whereby the uncured joining agent comprises monomers of a (meth) acrylic acid alkyl ester, and the cured joining agent comprises at least one polymer of the (meth)acrylic acid alkyl ester;

characterized in that the uncured joining agent comprises at least 70% by weight (meth)acrylic acid alkyl ester monomers and maximally 30% by weight polymerized (meth)acrylic acid alkyl esters and in that an adhesion promoter is applied in order to establish a firmly bonded connection between the housing and the head part, whereby the adhesion promoter comprises at least a first functional group and a second functional group.

9. The method according to claim 8, characterized in that, in at least part of the adhesion promoter, a chemical bond is generated between the first functional group and at least one of the surfaces from the group of a contact surface of the housing and a connecting surface of the head part, and a chemical bond is generated between the second functional group and at least one polymer of the cured joining agent, whereby the contact surface of the housing and the connecting surface of the head part are those respective surfaces of the housing and head part that contact when the housing and head part are bonded together.

10. The method according to claim 9, characterized in that the chemical bond between the contact surface of the housing and/or the connecting surface of the head part and the first functional group is established through thiol-modified triazine matrices and/or a phosphate group.

11. The method according to claim 8, characterized in that the second functional group is an alkylacrylate.

12. The method according to claim 11, characterized in that the second functional group is a methacrylate or an acrylate.

13. An active implantable medical device having a housing and a head part of the active implantable medical device, whereby the head part is configured to provide electrical contact for lead connectors to the active implantable medical device and the housing is configured to hermetically enclose at least one functional element of the medical device, the head part covers at least a part of the housing, and the housing and the head part are connected to each other in a firmly bonded connection through a cured joining agent, characterized in that the cured joining agent comprises at least one polymer of a (meth)acrylic acid alkyl ester and in that the housing and the head part are connected to each other in a firmly bonded manner through the cured joining agent and an adhesion promoter, in that the adhesion promoter comprises at least one bifunctional molecule, and in that, at least in part of the adhesion promoter, a chemical bond is established between a first functional group and at least one of the surfaces from the group of a contact surface of the housing and a connecting surface of the head part, and a chemical bond is established between a second functional group and at least one polymer of the cured joining agent, whereby the contact surface of the housing and the connecting surface of the head part are those respective surfaces of the housing and head part that contact when the housing and head part are bonded together.

14. The active implantable medical device according to claim 13, characterized in that at least one bifunctional molecule of the adhesion promoter comprises a spacer for spatial separation of the first functional group and the second functional group.

15. The active implantable device according to claim 13, characterized in that the firmly bonded connection between the housing and the head part has a combined tension and shear resistance between 20 MPa and 40 MPa.

16. The active implantable device according to claim 13, characterized in that the firmly bonded connection between the housing and the head part has a combined tension and shear resistance between 30 MPa and 40 MPa.

17. The active implantable device according to claim 13, characterized in that the housing and the head part of the active implantable device are connected, whereby an uncured joining agent that is arranged, at least in part, between the housing and the head part is transitioned into a cured joining agent to attain the firmly bonded connection, whereby the uncured joining agent comprises monomers of a (meth)acrylic acid alkyl ester, and the cured joining agent comprises at least one polymer of the (meth)acrylic acid alkyl ester.

18. The active implantable medical device according to claim 13, characterized in that the cured joining agent comprises at least 70% by weight polymer of (meth)acrylic acid alkyl esters and maximally 30% by weight (meth)acrylic acid alkyl ester monomers.

* * * * *